(12) United States Patent
Guterman et al.

(10) Patent No.: US 10,078,893 B2
(45) Date of Patent: Sep. 18, 2018

(54) AUTOMATIC LEFT VENTRICULAR FUNCTION EVALUATION

(75) Inventors: Hugo Guterman, Beer Sheva (IL); Noah Liel, Omer (IL); Marina Yaacobi, Rishon Lezion (IL)

(73) Assignee: DIA IMAGING ANALYSIS LTD, Be'er Sheva (IL)

( * ) Notice: Subject to any disclaimer, the term of this patent is extended or adjusted under 35 U.S.C. 154(b) by 414 days.

(21) Appl. No.: 13/977,877

(22) PCT Filed: Dec. 29, 2011

(86) PCT No.: PCT/IL2011/050084
§ 371 (c)(1),
(2), (4) Date: Jul. 1, 2013

(87) PCT Pub. No.: WO2012/090208
PCT Pub. Date: Jul. 5, 2012

(65) Prior Publication Data
US 2013/0278776 A1    Oct. 24, 2013

Related U.S. Application Data

(60) Provisional application No. 61/427,830, filed on Dec. 29, 2010.

(51) Int. Cl.
*G01S 15/89*     (2006.01)
*G06T 7/00*      (2017.01)
(Continued)

(52) U.S. Cl.
CPC ............ *G06T 7/0012* (2013.01); *A61B 8/065* (2013.01); *A61B 8/0883* (2013.01);
(Continued)

(58) Field of Classification Search
CPC ........ A61B 8/0883; G06T 2207/10132; G06T 2207/20112; G06T 2207/30048; G06T 7/0012; G06T 7/0083
(Continued)

(56) References Cited

U.S. PATENT DOCUMENTS 5,281,899 A    1/1994  Culp
5,360,006 A    11/1994 Geiser
(Continued)

FOREIGN PATENT DOCUMENTS

EP    0580128    1/1994
EP    1522875    4/2005
(Continued)

OTHER PUBLICATIONS

Delon et al. "A Non Parametric Approach for Histogram Segmentation"—2002.*
(Continued)

*Primary Examiner* — Jessica M Prince
*Assistant Examiner* — Kathleen Nguyen
(74) *Attorney, Agent, or Firm* — The Roy Gross Law Firm, LLC; Roy Gross

(57) ABSTRACT

A method for automatic left ventricular (LV) inner border detection, the method comprising: performing image mapping on an echocardiogram, to produce a multi-level image map; converting the image map into a binary image, by attributing pixels of one or more darker levels of the image map to the LV cavity and pixels of one or more lighter levels of the image map to the myocardium; applying a radial filter to contours of the myocardium in the binary image, to extract an approximate inner border of the LV; and performing shape modeling on the approximate inner border, to determine the LV inner border.

18 Claims, 12 Drawing Sheets

(51) Int. Cl.
*A61B 8/06* (2006.01)
*A61B 8/08* (2006.01)
*G06T 7/12* (2017.01)
*G06T 7/174* (2017.01)
*G06T 7/181* (2017.01)
*G06T 7/136* (2017.01)
*A61B 8/00* (2006.01)

(52) U.S. Cl.
CPC .......... *A61B 8/5223* (2013.01); *G06T 7/0016* (2013.01); *G06T 7/12* (2017.01); *G06T 7/136* (2017.01); *G06T 7/174* (2017.01); *G06T 7/181* (2017.01); *A61B 8/543* (2013.01); *G06T 2207/10016* (2013.01); *G06T 2207/10132* (2013.01); *G06T 2207/20032* (2013.01); *G06T 2207/30048* (2013.01)

(58) Field of Classification Search
USPC ........................................................ 348/163
See application file for complete search history.

(56) References Cited

U.S. PATENT DOCUMENTS

| | | | |
|---|---|---|---|
| 5,457,754 A | 10/1995 | Han | |
| 5,472,453 A | 12/1995 | Alt | |
| 5,797,396 A | 8/1998 | Geiser | |
| 6,106,466 A | 8/2000 | Sheehan | |
| 6,217,520 B1 | 4/2001 | He | |
| 6,346,124 B1 | 2/2002 | Geiser | |
| 6,447,453 B1 | 9/2002 | Roundhill | |
| 6,447,454 B1 | 9/2002 | Chenal | |
| 6,491,636 B2 | 12/2002 | Chenal | |
| 6,537,221 B2 | 3/2003 | Criton | |
| 6,545,678 B1 | 4/2003 | Ohazama | |
| 6,674,879 B1 | 1/2004 | Weisman | |
| 6,708,055 B2 | 3/2004 | Geiser | |
| 6,716,175 B2 | 4/2004 | Geiser | |
| 6,858,007 B1* | 2/2005 | Akselrod | A61B 6/466 128/916 |
| 7,008,564 B2 | 3/2006 | Harrup | |
| 7,022,073 B2 | 4/2006 | Fan | |
| 7,041,061 B2 | 5/2006 | Kramer | |
| 7,065,400 B2 | 6/2006 | Schechter | |
| 7,092,759 B2 | 8/2006 | Nehls | |
| 7,343,031 B2 | 3/2008 | Pedrizzetti | |
| 7,347,821 B2 | 3/2008 | Skyba | |
| 7,450,746 B2 | 11/2008 | Yang | |
| 7,603,154 B2 | 10/2009 | Noble | |
| 2002/0072670 A1 | 6/2002 | Chenal | |
| 2002/0072671 A1* | 6/2002 | Chenal | A61B 6/463 600/450 |
| 2002/0072672 A1 | 6/2002 | Roundhill | |
| 2002/0072674 A1 | 6/2002 | Criton | |
| 2002/0151793 A1 | 10/2002 | Geiser | |
| 2003/0009098 A1 | 1/2003 | Jack | |
| 2003/0038802 A1 | 2/2003 | Johnson | |
| 2003/0153823 A1* | 8/2003 | Geiser | G06T 7/0012 600/407 |
| 2003/0160786 A1 | 8/2003 | Johnson | |
| 2003/0187362 A1 | 10/2003 | Murphy | |
| 2004/0009404 A1 | 1/2004 | Harrup | |
| 2004/0015081 A1 | 1/2004 | Kramer | |
| 2004/0049115 A1 | 3/2004 | Murphy | |
| 2004/0049116 A1 | 3/2004 | Murphy | |
| 2004/0143189 A1 | 7/2004 | Lysyansky | |
| 2004/0153128 A1 | 8/2004 | Suresh | |
| 2004/0176678 A1 | 9/2004 | Murphy | |
| 2004/0176679 A1 | 9/2004 | Murphy | |
| 2004/0267125 A1* | 12/2004 | Skyba | A61B 8/0858 600/443 |
| 2005/0020903 A1 | 1/2005 | Krishnan | |
| 2005/0020929 A1 | 1/2005 | Murphy | |
| 2005/0043609 A1 | 2/2005 | Murphy | |
| 2005/0043895 A1 | 2/2005 | Schechter | |
| 2005/0059876 A1 | 3/2005 | Krishnan | |
| 2005/0071003 A1 | 3/2005 | Ku | |
| 2005/0074153 A1 | 4/2005 | Pedrizzetti | |
| 2005/0075567 A1 | 4/2005 | Skyba | |
| 2005/0075727 A1* | 4/2005 | Wheatley | A61F 2/2457 623/2.17 |
| 2005/0080327 A1 | 4/2005 | Jenkins | |
| 2005/0106255 A1 | 5/2005 | Ku | |
| 2005/0187461 A1 | 8/2005 | Murphy | |
| 2005/0228276 A1 | 10/2005 | He | |
| 2005/0254708 A1 | 11/2005 | Jolly | |
| 2006/0034508 A1 | 2/2006 | Zhou | |
| 2006/0074312 A1 | 4/2006 | Georgescu | |
| 2006/0116731 A1 | 6/2006 | Kramer | |
| 2006/0173317 A1 | 8/2006 | Lee | |
| 2006/0235480 A1 | 10/2006 | Schecter | |
| 2006/0247545 A1 | 11/2006 | St. Martin | |
| 2007/0014452 A1 | 1/2007 | Suresh | |
| 2007/0016019 A1 | 1/2007 | Salgo | |
| 2007/0078344 A1 | 4/2007 | Rafter | |
| 2007/0088209 A1 | 4/2007 | Jyrki | |
| 2007/0088213 A1 | 4/2007 | Poland | |
| 2007/0263915 A1* | 11/2007 | Mashiach | G06K 9/342 382/130 |
| 2008/0008369 A1 | 1/2008 | Koptenko | |
| 2008/0107302 A1 | 5/2008 | Zhou | |
| 2008/0181479 A1* | 7/2008 | Yang | A61B 5/0456 382/131 |
| 2008/0263691 A1 | 10/2008 | Metzger | |
| 2008/0281182 A1 | 11/2008 | Rabben | |
| 2009/0201291 A1* | 8/2009 | Ziv | A61B 5/055 345/424 |
| 2010/0100392 A1 | 4/2010 | Rothman | |

FOREIGN PATENT DOCUMENTS

| | | |
|---|---|---|
| EP | 1769830 | 4/2007 |
| JP | 2002175533 | 6/2002 |
| JP | 2009028096 | 2/2009 |
| WO | 9119457 | 12/1991 |
| WO | 9641312 | 12/1996 |
| WO | 9949775 | 10/1999 |
| WO | 9955233 | 11/1999 |
| WO | 0245586 | 6/2002 |
| WO | 0245587 | 6/2002 |
| WO | 2004008558 | 1/2004 |
| WO | 2004008955 | 1/2004 |
| WO | 2004068406 | 8/2004 |
| WO | 2004070553 | 8/2004 |
| WO | 2005001769 | 1/2005 |
| WO | 2005020025 | 3/2005 |
| WO | 2005030057 | 4/2005 |
| WO | 2005039418 | 5/2005 |
| WO | 2005046473 | 5/2005 |
| WO | 2005050252 | 6/2005 |
| WO | 2005065028 | 7/2005 |
| WO | 2005070988 | 8/2005 |
| WO | 2005081168 | 9/2005 |
| WO | 2006044996 | 4/2006 |
| WO | 2006085268 | 8/2006 |
| WO | 2006114734 | 11/2006 |
| WO | 2007022133 | 2/2007 |
| WO | 2007090093 | 8/2007 |
| WO | 2008026022 | 3/2008 |
| WO | 2010004479 | 1/2010 |

OTHER PUBLICATIONS

Bouguet (1994) Pyramidal implementation of the Affine Lucas-Kanade feature tracker, description of the algorithm. Technical report, Intel Corporation Research Labs.

Carolyn and Solomon (2006) A clinician's guide to tissue doppler imaging. Circulation 113(10): e396-e398.

Kass et al., (1988) Snakes: active contour models. International Journal on Computer Vision 1(4): 321-331.

(56) References Cited

OTHER PUBLICATIONS

Lang et al., (2005) Recommendations for chamber Quantification: A Report from the American Society of Echocardiography's Guidelines and Standards Committee and the Chamber Quantification Writing Group, Developed in Conjunction with the European Association of Echocardiography, a Branch of the European Society of Cardiology. J Am Soc Echocardiogr 18(12): 1440-63.

McInerney and Terzopoulos (1996) Deformable models in medical image analysis: a survey. Medical Image Analysis 1(2): 91-108.

Melton et al., (1983) Automatic real-time endocardial edge detection in two-dimensional echocardiography. Ultrason Imaging 5(4): 300-7.

Ohyama et al., (2000) Automatic left ventricular endocardium detection in echocardiograms based on ternary thresholding method. IEEE, Pattern Recognition, 2000. Proceedings. 15th International Conference on 4: 320-323.

Otsu (1979) A threshold selection method from gray-level histograms. IEEE Transactions on Systems, Man and Cybernetics 9(1): 62-66.

Saputro et al., (2010) Motion estimation along the myocardial boundary using boundary extraction and optical flow. Proceedings of the World Congress on Engineering 2010 vol. I: 677-680.

Sigit (2009) Automatic border detection of cardiac cavity images using boundary and triangle equation. TENCON 2009—2009 IEEE Region 10 Conference, pp. 1-4.

Sussner et al., (1995) Contour detection using artificial neuronal network presegmentation. Proc Computers in Cardiology pp. 737-740, Vienna.

Yaacobi (2005) Automatic LV function evaluation from echocardiographic images. M.Sc. Thesis. Ben-Gurion University of the Negev, Israel.

Mottram and Marwick (2005) Assessment of diastolic function: what the general cardiologist needs to know. Heart 91 (5): 681-95.

Yaacobi et al., (2008) Simultaneous Left Atrium Volume Tracking from Echocardiographic Movies, IEEE1 25th Convention, pp. 403-407.

European Search Report—11852693.8 of PCT/IL/2011/050084 Completed Aug. 18, 2017; dated Aug. 31, 2017 12 pages.

Anonymous: "email publication date of M.Sc. thesis by Yaacobi." Jul. 26, 2017, pp. 1-3.

* cited by examiner

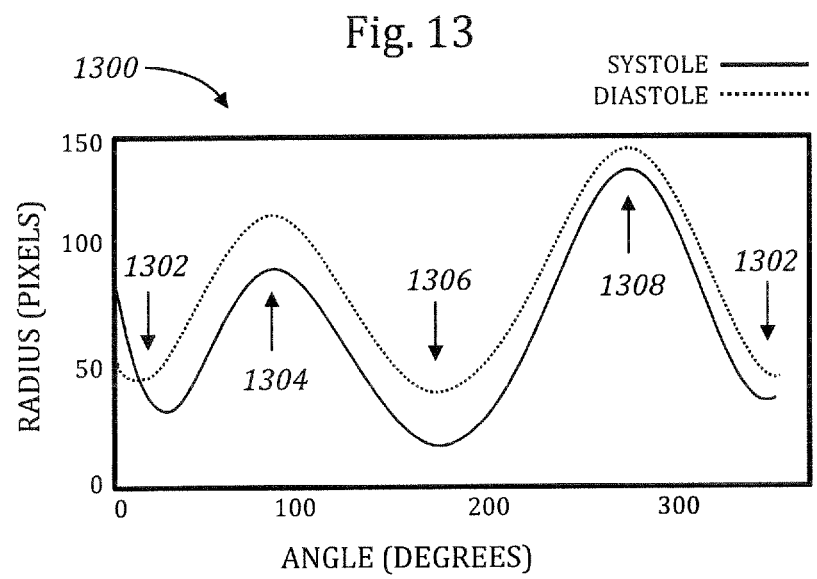
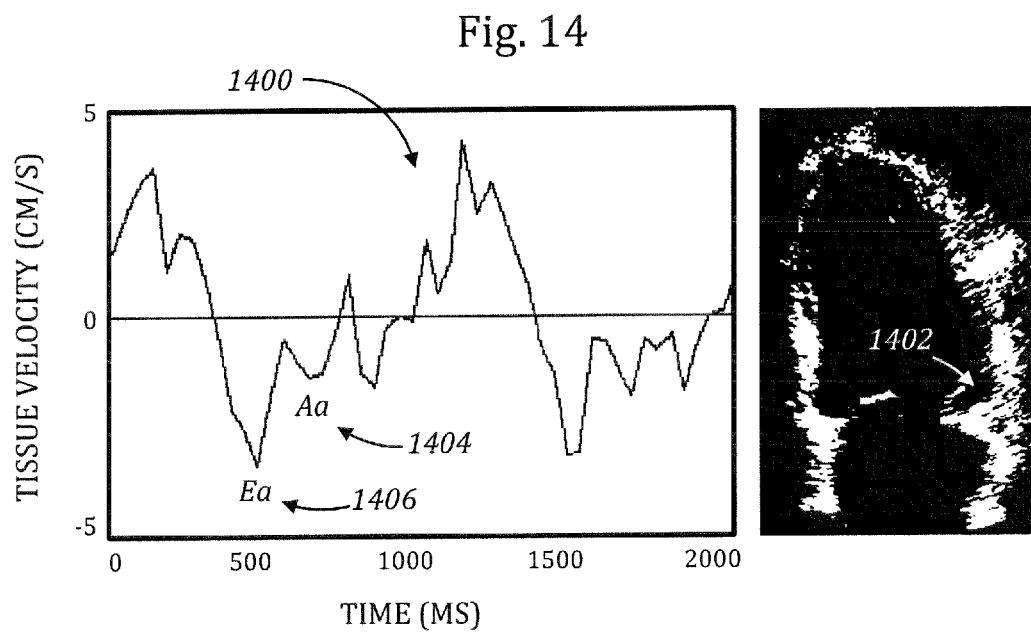

AUTOMATIC LEFT VENTRICULAR FUNCTION EVALUATION

RELATED APPLICATION DATA

This application is a U.S. National Stage of International Application No. PCT/IL2011/050084, filed Dec. 29, 2011, which claims the benefit of U.S. Provisional Application No. 61/427,830, filed Dec. 29, 2010, the contents of each of which are herein expressly incorporated by reference for all purposes.

FIELD OF THE INVENTION

The invention relates to automatic left ventricular (LV) function evaluation.

BACKGROUND OF THE INVENTION

Echocardiography is an important, widely-used imaging technique for clinical diagnosis of heart diseases. Due to its low cost and non-invasive nature, ultrasonic imaging is an integral part of modern diagnostic-imaging facilities, allowing qualitative and quantitative performance evaluation of the cardiovascular system, including LV function.

Since many of the cardiac diseases in adults result in abnormalities of LV function, the LV function evaluation is a very important part of almost every echocardiographic examination. LV systolic function parameters are usually examined qualitatively by experts, and estimated by eyeballing. Global quantitative LV evaluation, when performed, is often done from two planes of the heart, namely—the four chamber and the two chamber planes, by selecting, from each plane, two frames of the cardiac cycle, at the end of the diastole (ED) and at the end of the systole (ES), after which manual tracing of the LV border is done. LV ED and ES volumes and ejection fraction (EF) are calculated by specific algorithms. As this technique is operator-dependent and time consuming, it is rarely used in everyday practice.

Automatic LV border detection has been, therefore, the subject of many echocardiographic researches in the past decade. Automatic LV border detection would not only allow fast, accurate, and robust echocardiographic evaluation of the LV systolic function, but would also provide additional quantitative information about the LV function during the entire cardiac cycle.

Automatic LV contour detection can be described as a segmentation problem—the problem of separating muscle from blood, which is often considered to be a difficult task in ultrasound images. LV true contours might be confused with local false edges caused by speckle noise which is superimposed on the image and hides the target tissue, or the true contours can be vague and partially missing.

A prominent approach to LV border detection in the literature is based on a simple assumption that different parts composing the image are delimited by borders. Hence, border pixels (edges) can be obtained by extraction and grouping of points at the transition between different parts in the image, to form closed boundaries.

Many algorithms have been proposed for LV border detection and tracking, using distinct approaches. Some of the methods are related to the family of deformable models, in which the parametric contour is deformed over the cardiac cycle using an initial contour provided from a user input. See McInerney T. and Terzopoulos D., "*Deformable Models in Medical Image Analysis: A Survey*", Medical Image Analysis 1 (1996) 91-108, which discusses an application of the "snakes" method proposed by M. Kass, A. Witkin, D. Terzopoulos, "Snakes: Active Contour Models", *International Journal on Computer Vision*, vol. 1(4), pp. 321-331, 1988.

Other methods are based on fitting a detected border to a pre-defined shape model, but often require a user's input of at least three points. See, for example, U.S. Published Patent Application No. 2002/0072671 to Chenal et al., which discloses acquiring an ultrasonic image, locating an anatomical landmark in the image, and fitting a trace to a tissue border related to the anatomical feature.

Further methods use neural networks to classify each pixel in the image, based on features extracted from co-occurrence matrix. See, for example, M. Sussner, N. Budil, T. Strohmer. "Contour detection using artificial neuronal network presegmentation", *Proc. Computers in Cardiology*, pp. 737-740, Vienna 1995.

In addition to global LV evaluation, the segmental wall motion performance is also frequently evaluated. The evaluation of the contraction of different LV wall segments is important, as patients with ischemic heart disease (IHD) usually have segmental rather than global wall contraction abnormalities. Recognition of this abnormality is of great clinical importance. Segmental wall motion evaluation is usually assessed in a qualitative way by eyeballing, which is very dependent on the experience of the expert. Therefore, quantitative segmental wall motion evaluation is of great importance.

Tissue Doppler imaging (TDI) is a quantitative echocardiographic technique that uses Doppler principles to measure the velocity of myocardial motion. See Carolyn Y. Ho and Scott D. Solomon, "*A Clinician's Guide to Tissue Doppler Imaging*", Circulation 2006; 113:e396-e398. Doppler echocardiography relies on detecting the shift in frequency of ultrasound signals reflected from moving objects. Conventional Doppler techniques assess the velocity of blood flow. In TDI, the same Doppler principles are used to quantify myocardial tissue motion, and measure Doppler strain and strain rate.

As with all Doppler techniques, TDI measures motions parallel to the direction of the ultrasound beam; further, the Doppler-based methods obtain tissue velocity information from fixed beam position, which may not be accurate since the heart is constantly moving. Therefore, TDI is not conventionally used for regional wall motion evaluation; however, it was found to be helpful in evaluating diastolic function by measuring the overall longitudinal left ventricular (LV) relaxation at the mitral annulus.

Non-Doppler 2D strain imaging is a competitive method in which stable features inside the myocardium are tracked through the cardiac cycle to provide strain rate information representing muscle contraction and relaxation in 2D. See, for example, U.S. Published Patent Application No. 2004/0143189 to Lysyansky et al. Several difficulties may arise when using such methods. The spatial pattern of the features retains its probability for at least two frames, and perhaps even more in the absence of speckle noise. Therefore, the features must be reselected at some frequency and fitted to some motion model. A motion model should be carefully used, since wall motion pattern changes with the impairment of the tissue and influenced by other physical parameters, such as hemodynamic forces.

SUMMARY OF THE INVENTION

There is provided, in accordance with an embodiment, a method for automatic left ventricular (LV) inner border detection, the method comprising: performing image mapping on an echocardiogram, to produce a multi-level image map; converting the multi-level image map into a binary image, by attributing pixels of one or more darker levels of the image map to the LV cavity and pixels of one or more lighter levels of the image map to the myocardium; applying a radial filter to contours of the myocardium in the binary image, to extract an approximate inner border of the LV; and performing shape modeling on the approximate inner border, to determine the LV inner border.

There is further provided, in accordance with an embodiment, an ultrasonic imaging device, comprising: an ultrasonic probe configured to acquire an echocardiogram; and a processing unit connected to said probe and configured to automatically closely approximate an inner border of the left ventricular (LV) appearing in the echocardiogram, the approximation being based on shape modeling of a pre-processed echocardiogram of the LV.

In some embodiments, the multi-level image map comprises a 3-level image map, and wherein the one or more darker levels of the image map comprise two darker levels and the one or more lighter levels of the image map comprise one lighter level.

In some embodiments, the method further comprises, prior to performing the image mapping, automatically detecting a region of interest in the echocardiogram, wherein the region of interest encloses the LV.

In some embodiments, the automatic detection of the region of interest comprises: producing an inverted binary version of the echocardiogram; computing a column histogram of white pixels in the inverted binary version; and defining an area delimited between two minimum points of the column histogram as the region of interest.

In some embodiments, the image mapping comprises segmenting the echocardiogram using piece-wise histogram equalization.

In some embodiments, the piece-wise histogram equalization comprises determining a central axis of the LV and dividing the LV appearing in the echocardiogram, based on entropy levels in the histogram, into a plurality of rectangular segments situated on lateral and septal sides of the central axis.

In some embodiments, the echocardiogram comprises an apical view echocardiogram.

In some embodiments, the apical view comprises a two-chamber apical view, wherein optionally, the multi-level image map comprises a 3 to 5-level image map.

In some embodiments, the apical view comprises a four-chamber apical view, wherein optionally, the multi-level image map comprises a 3-level image map, and wherein the one or more darker levels of the image map comprise two darker levels and the one or more lighter levels of the image map comprise one lighter level.

In some embodiments, the echocardiogram comprises a long-axis view echocardiogram.

In some embodiments, the echocardiogram comprises a short-axis view echocardiogram.

In some embodiments, the method further comprises, prior to performing the image mapping, reducing noise in the echocardiogram.

In some embodiments, the reduction of the noise comprises employing a median filter on the echocardiogram.

In some embodiments, the method further comprises, prior to applying the radial filter, refining the binary image using binary morphology.

In some embodiments, the method further comprises, prior to applying the radial filter, clearing pixel blob residues located in the LV cavity.

In some embodiments, the method further comprises, prior to performing the shape modeling, calculating polar coordinates of the approximate inner border of the LV.

In some embodiments, the shape modeling comprises $6^{th}$ order polynomial interpolation performed on the polar coordinates of the approximate inner border of the LV.

In some embodiments, the echocardiogram comprises an end-diastole echocardiogram, and wherein the method further comprises tracking the determined LV inner border over consecutive echocardiograms which include an end-systole echocardiogram.

In some embodiments, at least one of a moment of the end-diastole and a moment of the end-systole is determined based on a preliminary tracking step performed on the determined LV inner border, over consecutive echocardiograms which include the end-diastole and end-systole moments.

In some embodiments, at least one of a moment of the end-diastole and a moment of the end-systole is determined based on an electrocardiogram (ECG) signal associated with the echocardiograms of the cardiac cycle.

In some embodiments, the method further comprises calculating an ejection fraction (EF) of the LV using the Simpson method, based on a ratio between calculated volumes of the end-diastole echocardiogram and the end-systole echocardiogram for each heartbeat.

In some embodiments, the tracking comprises tracking using a pyramidal optical flow method.

In some embodiments, the method further comprises performing $4^{th}$ order polynomial interpolation on the approximate inner border at a septal side of the LV, and parabolic interpolation on the approximate inner border at a lateral side of the LV.

In some embodiments, the method further comprises computing a volume of the LV along at least some of the consecutive echocardiograms, to create a volume curve of the cardiac cycle.

In some embodiments, the method further comprises computing, based on the volume curve, a filling rate curve of the LV.

In some embodiments, the method further comprises computing, based on the filling rate curve, a global diastolic function parameter selected from the group consisting of: a rapid filling rate peak parameter ("E"), an atrial filling rate peak parameter ("A"), an "E"/"A" ratio, an acceleration time to "E" (from "Mo"), a deceleration time from "E" ("DT"), and an isovolumetric relaxation time ("IVRT").

In some embodiments, the method further comprises computing, based on the filling rate curve, a global systolic function parameter selected from the group consisting of: end-diastole volume ("EDV"), end-systole volume ("ESV"), ejection fraction ("EF") and stroke volume ("SV").

In some embodiments, the method further comprises detecting regional wall motion abnormalities of the LV by deriving an angular displacement curve of the determined LV inner border.

In some embodiments, the method further comprises computing, by deriving an angular displacement curve of the determined LV inner border, a global diastolic function selected from the group consisting of: Ea and Aa.

In some embodiments, said processing unit is further configured to: perform image mapping on the echocardiogram, to produce a multi-level image map; convert the multi-level image map to a binary image, by attributing pixels of one or more darker levels of the image map to the LV cavity and pixels of one or more lighter levels of the image map to the myocardium; and apply a radial filter to contours of the myocardium in the binary image, to extract an approximate inner border of the LV.

In some embodiments, said processing unit is further configured to, prior to performing the image mapping, automatically detect a region of interest in the echocardiogram, wherein the region of interest encloses the LV.

In some embodiments, said processing unit is further configured to, prior to performing the image mapping, reduce noise in the echocardiogram.

In some embodiments, the reduction of the noise comprises employing a median filter on the echocardiogram.

In some embodiments, said processing unit is further configured to, prior to applying the radial filter, refine the binary image using binary morphology.

In some embodiments, said processing unit is further configured to, prior to applying the radial filter, clear pixel blob residues located in the LV cavity.

In some embodiments, said processing unit is further configured to, prior to performing the shape modeling, calculate polar coordinates of approximate inner border of the LV.

In some embodiments, at least one of a moment of the end-diastole and a moment of the end-systole is determined by said processing unit based on an electrocardiogram (ECG) signal associated with the echocardiograms of the cardiac cycle.

In some embodiments, at least one of a moment of the end-diastole and a moment of the end-systole is determined by said processing unit based on a preliminary tracking step performed on the determined LV inner border, over consecutive echocardiograms which include the end-diastole and end-systole moments.

In some embodiments, said processing unit is further configured to calculate an ejection fraction (EF) of the LV using the Simpson method, based on a ratio between calculated volumes of the end-diastole echocardiogram and the end-systole echocardiogram for each heartbeat.

In some embodiments, said processing unit is further configured to perform $4^{th}$ order polynomial interpolation on the approximate inner border at a septal side of the LV, and parabolic interpolation on the approximate inner border at a lateral side of the LV.

In some embodiments, said processing unit is further configured to compute a volume of the LV along at least some of the consecutive echocardiograms, to create a volume curve of the cardiac cycle.

In some embodiments, said processing unit is further configured to compute, based on the volume curve, a filling rate curve of the LV.

In some embodiments, said processing unit is further configured to compute, based on the filling rate curve, a global diastolic function parameter selected from the group consisting of: a rapid filling peak velocity parameter ("E"), an atrial filling peak velocity parameter ("A"), an "E"/"A" ratio, an acceleration time to "E" (from "Mo"), a deceleration time from "E" ("DT"), and an isovolumetric relaxation time ("IVRT").

In some embodiments, said processing unit is further configured to compute, based on the filling rate curve, a global systolic function parameter selected from the group consisting of: end-diastole volume ("EDV"), end-systole volume ("ESV"), ejection fraction ("EF") and stroke volume ("SV").

In some embodiments, said processing unit is further configured to detect regional wall motion abnormalities of the LV by deriving an angular displacement curve of the determined LV inner border.

In some embodiments, said processing unit is further configured to compute, by deriving an angular displacement curve of the determined LV inner border, a global diastolic function selected from the group consisting of: Ea and Aa.

There is further provided, in accordance with an embodiment, a method for automatic modeling of a left ventricular (LV) inner border, the method comprising automatically modeling the shape of the inner border based on $6^{th}$-order polynomial interpolation performed on polar coordinate points crudely marking the inner border.

There is further provided, in accordance with an embodiment, an apparatus comprising a processing unit configured to automatically model a left ventricular (LV) inner border, based on $6^{th}$-order polynomial interpolation performed on polar coordinate points crudely marking the inner border.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 13 shows an overlay of a diastole displacement curve and a systole displacement curve;

FIG. 14 shows an angular displacement derivative over time, of a point on the LV inner border located at the lateral side of the mitral annulus;

DETAILED DESCRIPTION

An aspect of the invention relates to a method for automatically detecting, in a cardiogram, the inner borders of the left ventricle (LV). The method includes advantageous shape modeling of the LV shape, based on polynomial interpolation, in a polar coordinate system, of approximate borders obtained using image processing techniques. Namely, the polynomial interpolation is performed on points, in polar coordinates, which crudely mark the inner border. Optionally, the polynomial interpolation is based on a $6^{th}$ order polynomial, which has been presently found to define the LV borders with great accuracy.

The image processing techniques used to determine the approximate borders, may include a series of actions performed on the original echocardiogram, for the purpose of bringing it to a preparedness level which allows for efficient application of the polynomial interpolation.

An optional, advantageous, preliminary step may include the automatic detection, in the echocardiogram, of a region of interest (ROI) which encloses the LV. By virtue of this ROI detection, the present method may be applied to the echocardiogram directly, without the need for human intervention in the preliminary definition of the relevant area.

Following the detection of the LV borders in a first echocardiogram, which is optionally of the end-diastole (ED), the borders may be tracked along a series of consecutive echocardiograms of the same cardiac cycle, up to the end-systole (ES). For better statistically-significant results, the tracking my further extend over additional cardiac cycle(s), up to the entirety of the received echocardiograms. Then, the detected borders at the ED and the ES may be used for calculating the LV's ejection fraction (EF), optionally using the Simpson method.

The results of the tracking may be further used to create a temporal volume curve of the LV, and, optionally, a filling rate curve derived from the volume curve. Moreover, the tracking may enable computing a set of parameters indicating systolic and/or diastolic function. At least some of these parameters usually require the use of a Doppler ultrasound device, but are made possible here by virtue of the advantageous tracking. Such parameters may include, for example, a peak filling rate of the rapid filling phase (parameter "E"), a peak filling rate of the atrial contraction phase (parameter "A"), an E/A ratio, an acceleration time a deceleration, an isovolumetric relaxation time (IVRT), and "TDI" parameters such as "Ea" wave, "Aa" wave, etc.

Furthermore, detection of regional wall motion abnormalities of the LV is also disclosed herein. This detection may be based on a comparison between locations of segments of the LV inner border in two or more consecutive echocardiograms, as well as on tissue velocity in various segment points.

Figure 1:
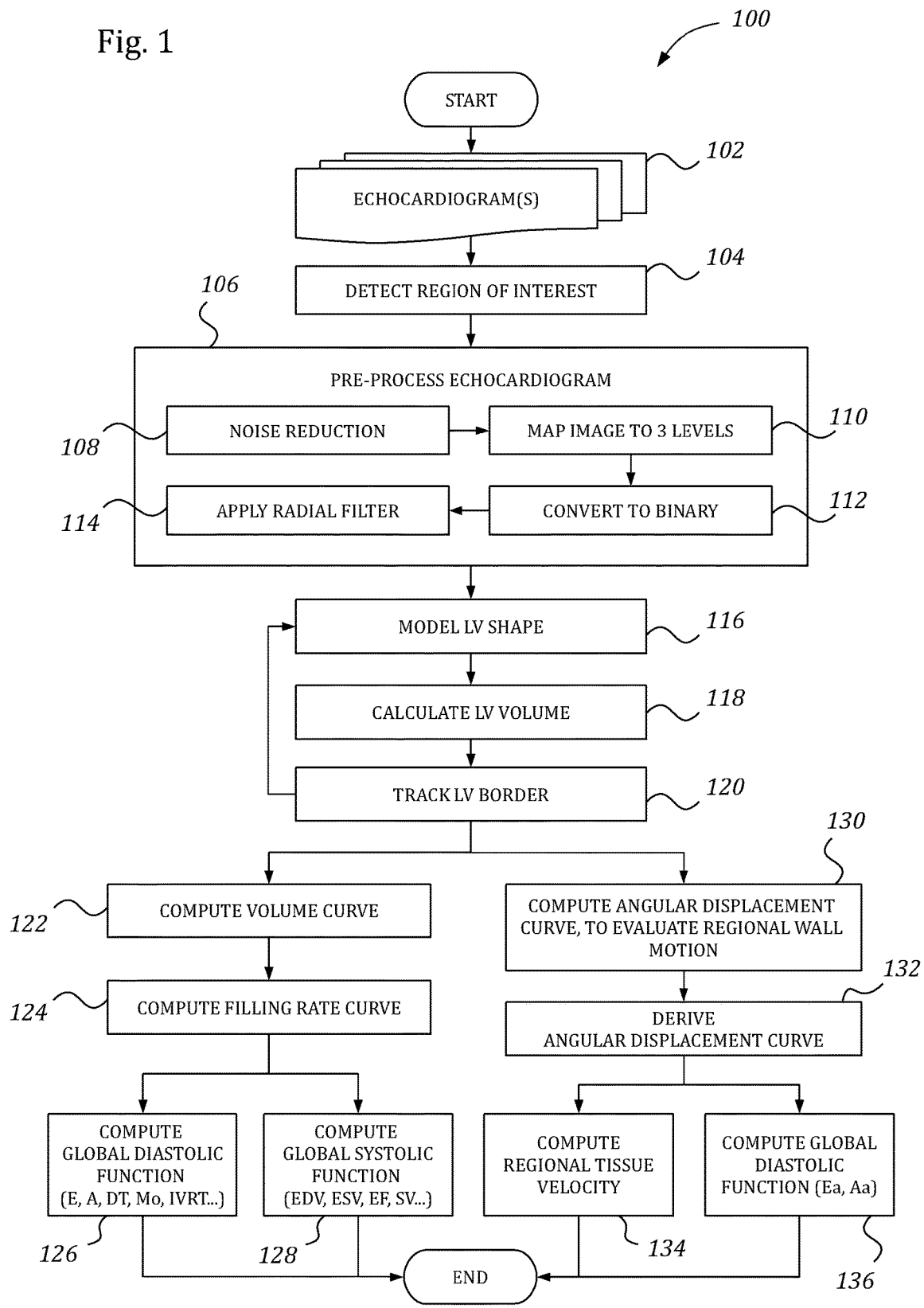
FIG. 1 shows a flow chart of a method for automatic LV inner border detection.

Reference is now made to FIG. 1, which shows a flow chart of a method 100 for automatic left ventricular (LV) inner border detection, in accordance with an embodiment.

Initially, a set of one or more echocardiograms 102 (also referred to as "images") is provided, such as from an ultrasound imaging device. Optionally, one of these echocardiograms 102, the one that shows the end-diastole moment, is selected as the initial echocardiogram for LV border detection. The end-diastole echocardiogram usually contains the maximal amount of blood and exhibits the least amount of motion, and hence the least amount of phenomena like smearing and noise. The LV border is initially detected in this end-diastole cardiogram, and only later in the other cardiograms of the cardiac cycle(s).

The end-diastole moment may be identified by performing a first, preliminary pass of blocks 106-120 (further discussed below) of method 100, in order to be able to estimate the LV volume in each of echocardiograms 102, assuming that the echocardiogram exhibiting the largest volume is of the end-diastole moment. It should be noted, however, that since this preliminary pass begins at an arbitrary echocardiogram, which is likely not the end-diastole echocardiogram, the results of this pass are probably inaccurate and cannot be relied upon. Hence, the LV volumes estimated during this preliminary pass are used only for the end-diastole moment determination, which then, by virtue of starting with the end-diastole echocardiogram, enables a much more reliable second pass.

Another alternative for determining the end-diastole moment is by relying on an electrocardiogram (ECG) signal which is associated with the echocardiogram, or is embedded in the echocardiographic images themselves.

For simplicity of presentation, the term "echocardiogram 102", as it appears in the following description, related to the end-diastole echocardiogram. Still, it is explicitly meant that various steps of method 100 may be performed on echocardiograms of other stages of the cardiac cycle.

Figure 2:
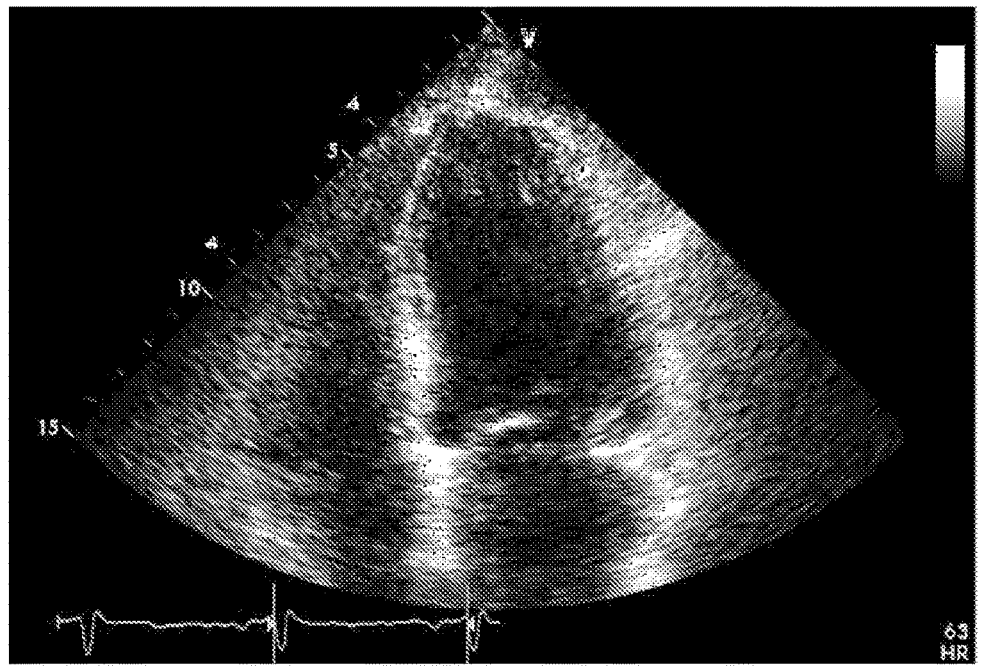
FIG. 2 shows an exemplary apical 4-chamber view echocardiogram.

FIG. 2 shows an exemplary echocardiogram 200, as it is typically received from an ultrasound imaging device. The echocardiograms discussed herein, such as echocardiogram(s) 102 of FIG. 1, are optionally captured at an apical approach of the ultrasonic probe, which shows the heart in a four chambers apical view. The apical view may be of the four chambers or of a different apical plane, such as a two-chamber plane. Method 100 of FIG. 1, however, applies also to other planes of the heart including short-axis plane and long-axis plane echocardiograms, with some adjustment of parameters. In either case, the resulting echocardiograms show a greater area than what is needed for the LV inner border detection. Furthermore, the following steps of method 100 may rely on accurate definition of a working zone, and usually require the working zone to be limited to the LV area. Therefore, determination of a region of interest (ROI) in echocardiogram 102 may be needed. This may be performed either manually, or, much more advantageously, by a fully-automatic process, in accordance with an embodiment.

Figure 3:
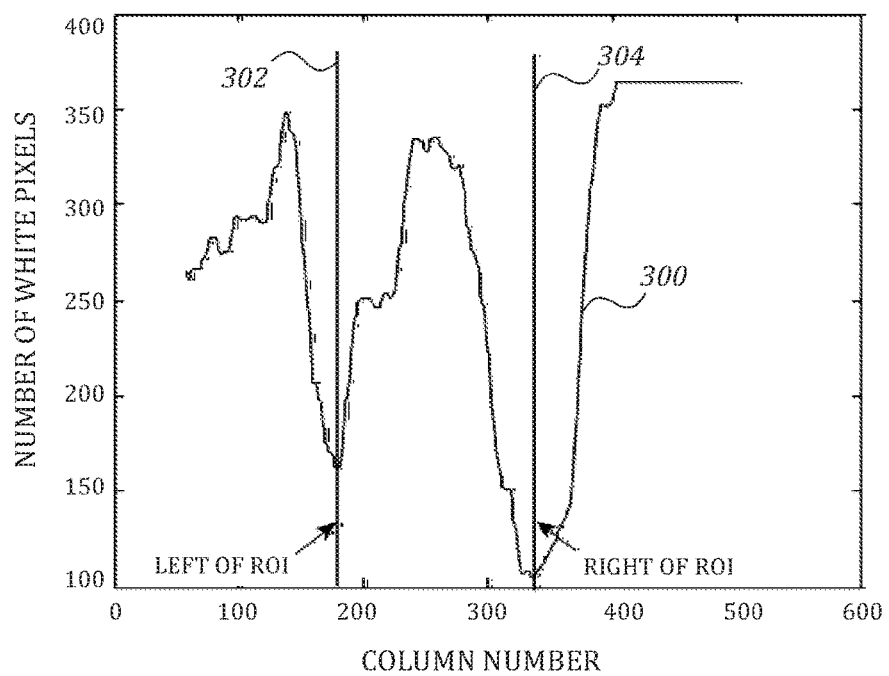
FIG. 3 shows a histogram indicating the number of white pixels in each column of an inverted binary echocardiogram.
Figure 4:
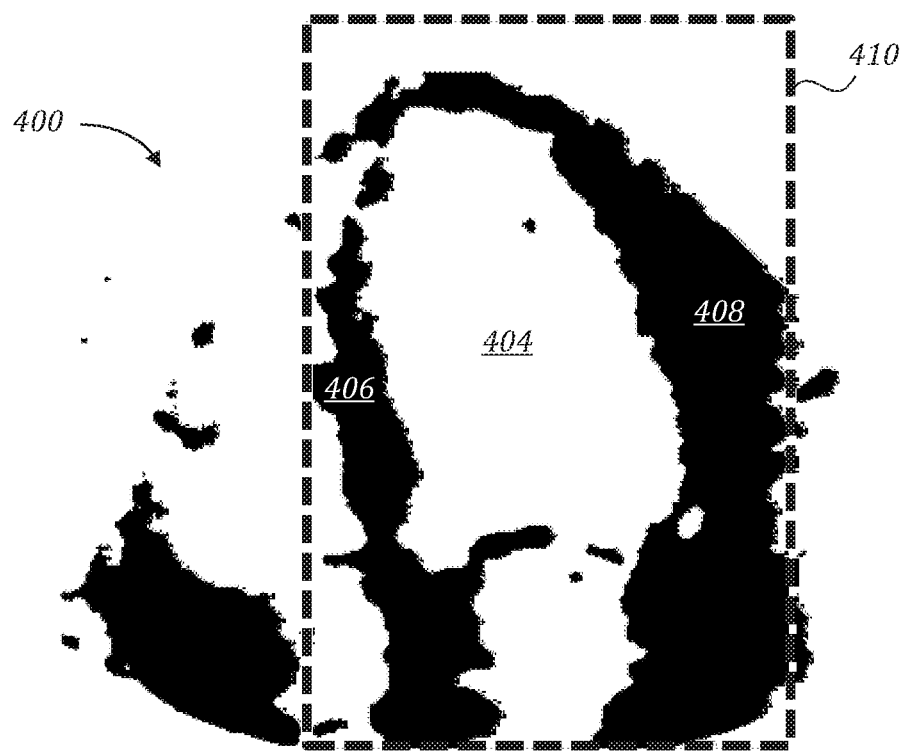
FIG. 4 shows a binary inverted image with a bounding box marking a region of interest enclosing the LV.

In an optional block 104, a region of interest (ROI) in echocardiogram 102 is automatically detected, and an image including only the ROI is produced. The ROI detection may be based on a number of steps. First, rough segmentation of the image may be performed, optionally by the Otsu method (see Nobuyuki Otsu. 1979. "A threshold selection method from gray-level histograms". *IEEE Trans. Sys., Man., Cyber.* 9: 62-66), resulting in a binary image. The binary image may be inverted, and a column histogram of the white pixels may be calculated. Reference is now made to FIG. 3, which shows a histogram 300 indicating the number of white pixels in each column of the echocardiogram. Histogram 300 exhibits two "minimums": one 302, which is the left end of the ROI (optionally the septal LV wall), and the other 304, which is the right end of the ROI (optionally the lateral LV wall). The area between the two minimums is the main LV cavity area. FIG. 4 shows this visually. A binary, inverted image 400 is shown, having the LV 402 (composed of a cavity area 404, a left edge 406 and a right edge 408) marked with a bounding box 410, being the ROI.

Reference is made back to FIG. 1. In a block 106, a series of image processing techniques may be applied to echocardiogram 102, bringing it to a preparedness level which allows for efficient shape modeling using polynomial interpolation, which finally determines the LV border. As to echocardiogram 102, it should be noted that the most common way to display ultrasonic patient examination is what is referred to as the B-mode. In B-mode ultrasound images, the echo amplitude is represented by the intensity (or gray level scale), while the term "image" refers to a two dimensional intensity function I(x,y), where x and y are spatial coordinates. Dark colors represent liquids and bright represent solids. In an LV image such as echocardiogram 102, the myocardium, which is characterized by bright colors, encloses the cavity which is filled with blood and therefore characterized by dark colors. For most ultrasound images, gray-level values are not well distributed and, in fact, the contrast often changes along the septal and lateral walls.

LV image segmentation in general and LV border detection in particular, may be therefore viewed as the process of separating tissue from blood. The series of image processing techniques of block 106 may begin with noise reduction 108. Speckle noise is a well-known interference in ultrasound images. Because of this noise, ultrasound images commonly exhibit granular appearance, in the form of "stains" of random sizes and intensities. This noise hides the target tissue and breaks its contour. Speckle noise reduction may be performed, in an embodiment, using a median filter, and results in an image being blurry especially around the edges and at the noisy parts. As a consequence, the filtered image is characterized by three main gray-level groups: bright (tissue), dark (blood) and intermediate (blurred noise).

Next, image mapping 110 may be performed on echocardiogram 102, to produce a multi-level image map, from which, optionally, the multiple levels are re-mapped to an image map of less levels. For example, the re-mapped image map may have its pixels mapped into three levels of intensity (or "darkness"): black, gray and white. Alternatively, image mapping may be done only once, directly to the desired final number of gray levels. Parameters such as wall thickness, wall orientation and/or the like may influence the decision how to perform the image mapping—such as how many times to repeat the mapping (if at all) and how many levels of gray should be produced in each mapping. By way of example, in a four-chamber view, three levels of gray may be appropriate, while in a two-chamber view, 3-5 levels of gray may be more suitable.

In general terms, the distribution of pixel values in a gray-level intensity image can be represented by a gray-level histogram defined as h(n)=k(g), (0≤g≤1, 1≤n≤256), where k is the number of gray-levels g in the image, and h is the normalized image histogram.

Histogram equalization is a well known contrast enhancement method which maps an M×N input image with L gray level values to a uniformly distributed output image, with the desired histogram of the form:

$$h_d(n) = \frac{M \times N}{L}, \quad (1)$$

$$(1 \le n \le L)$$

The present image mapping 110 may include segmentation of echocardiogram 102, simultaneously with pixel mapping using piece-wise histogram equalization. During the segmentation process, echocardiogram 102 may be divided into two halves with respect to the apex. When the view is of the apical four chamber type, echocardiogram 102 may be divided into septal and lateral halves. Each half may further be sub-divided into smaller regions according to the change in entropy. Entropy is defined by the inner product as: $E = -h^{Transpose}(\log(h))$, where h is the normalized image histogram. The threshold for homogenous region may be empirically selected. A region is defined as homogenous when $E - E_{start} < 1$, where E is the total entropy of the region and $E_{start}$ is the initial entropy of the region. Each homogenous region is equalized into, for example, three levels, as shown in Table 1:

TABLE 1

| Gray-Level | Color | Tissue |
| --- | --- | --- |
| 0 | Black | Blood |
| 0.5 | Gray | Noise and edges |
| 1 | White | Myocardium |

At the end of the image mapping 110, the different regions are combined into a single image, referred to herein, for illustrative reasons, as a 3-level image map, which is made of black, gray and while pixels, as shown in Table 1.

Note that since, in practice, full uniformity might change the image's nature, the image histogram is optionally mapped while keeping gray levels of the same value intact.

Next, the image map may be thresholded and converted 112 to a binary image, based on the rationale that noise is usually more apparent in the blood region than in the tissue region:

$$I_b = I_{hist} \begin{cases} 1 & \text{if } f(x, y) = T \\ 0 & \text{if } f(x, y) < T \end{cases} \quad (2)$$

where T=1, $I_b$ is the binary image and $I_{hist}$ is the 3-level image map which was the result of the image mapping. The thresholding, essentially, attributes black and gray pixels to the LV cavity and white pixels to the myocardium.

Optionally, the binary image is smoothed and refined using morphological opening and closing operators, and a blob filter is applied in order to clean residues of foreign tissue in the blood area.

Figure 6:
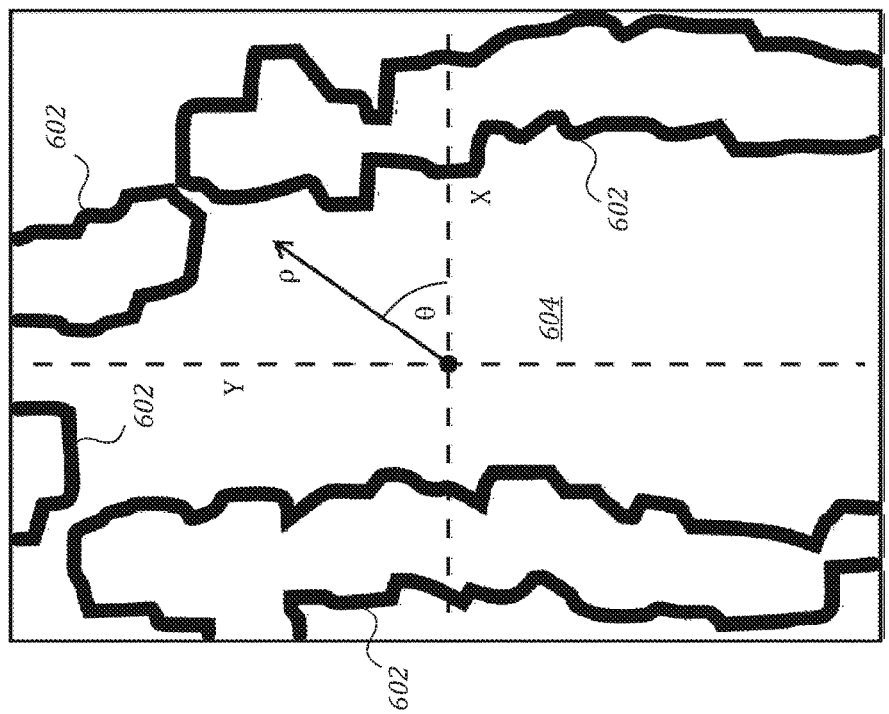
FIG. 6 shows extracted inner and outer contours of the myocardium.
Figure 5:
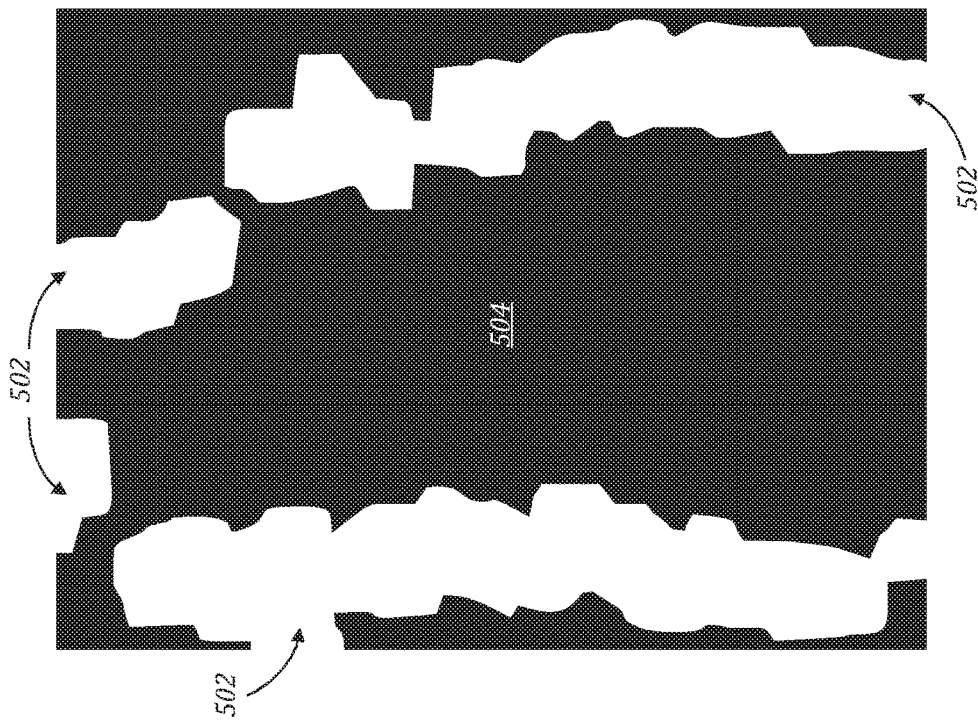
FIG. 5 shows a binary image, following thresholding of its 3-level mapped image predecessor.

Reference is now made to FIG. 5. The outcome, at this stage, is a binary image 500 which clearly shows the myocardium 502 and the LV cavity 504. Now, the contours of myocardium are extracted from the binary image, using an edge detection algorithm such as the Sobel operator. See Wikipedia contributors. "Sobel operator". *Wikipedia, The Free Encyclopedia*. Dec. 14, 2010, 02:38 UTC. Available at: http://en.wikipedia.org/w/index.php?title=Sobel_operator&oldid=402261909. Accessed Dec. 26, 2010. FIG. 6 shows the extracted contours 602. However, the extracted contours 602 encircle each part of the myocardium from all sides—both from the inner LV cavity 604 side and the opposite, outer side.

Next in method 100 of FIG. 1, in order to separate these inner and outer contours, a radial filter is applied 114 to them (or, more accurately, to their polar coordinates), and an approximate inner border of the LV is extracted. This is shown in FIG. 6. The extracted contours 602 are given by a Cartesian coordinate system (x,y). The Cartesian coordinates are translated to polar coordinates (ρ, θ), which indicate each point's angle and distance from a reference point—the image's center point 606 (CPT):

$$x_{polar} = x - x_{cpt} \quad (3)$$

$$y_{polar} = y - y_{cpt} \quad (4)$$

$$\rho = \sqrt{x_{polar}^2 + y_{polar}^2} \quad (5)$$

$$\theta = \tan^{-1}\left(\frac{y}{x}\right) \quad (6)$$

The radial filter is then applied, based on the notion that the radius of the outer contour points is greater than the radius of the inner contour points, at least within a limited angle range. Accordingly, the contours may be separated using one of two exemplary methods. A first method involves linear translation in the radials direction, away from the CPT, resulting in inner contour pixels having the value of one and outer contour pixels having the value of zero. A second method involves a $2^{nd}$-order radial filter, in which a $2^{nd}$-order polynomial, of the form $$P_n = a_0 + a_1\theta + a_2\theta^2 \quad (7)$$

is used to interpolate a line separating the inner and outer contours.

Figure 7:
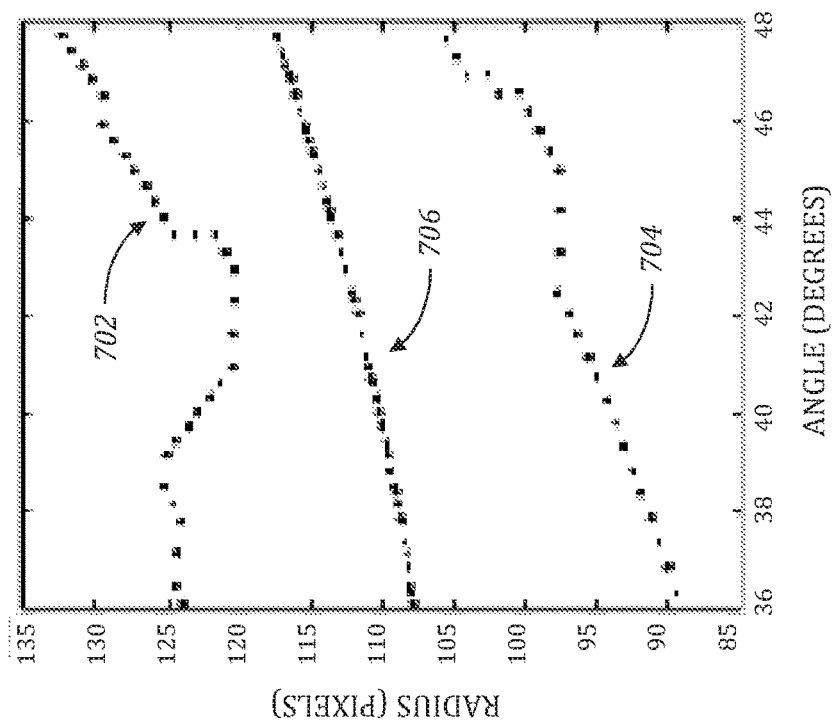
FIG. 7 shows a graph with results of radial filter application.

Reference is now made to FIG. 7, which shows a graph 700 of exemplary results of the radial filter application according to the second method, in radius as a function of angle. Graph is shown, for simplicity of presentation, only in the range of 36-48 degrees. Top points 702 represent the outer contour, bottom points 704 represent the inner contour, and middle points 706 illustrate the separator in between, which adheres to the $2^{nd}$-order polynomial. Accordingly, points 704 which approximate the inner border of the LV are extracted. Optionally, the number of extracted points is 25-35.

Back to FIG. 1. In a block 116, the extracted points, which approximate the LV inner border, are interpolated, in order to link the points and finally model and determine the LV inner border shape. The fact that method 100 does not make do with the extracted points, but proceeds to link the points in a way which accurately models the LV's shape, is greatly advantageous. Optionally, a $6^{th}$ order polynomial in polar coordinates, which has been tested empirically, is used as a shape model for contour point linking, resulting in an image with smooth contours:

$$P_6 = a_0 + a_1\theta^1 + a_2\theta^2 + \ldots + a_1\theta^6 \quad (8)$$

Figure 8:
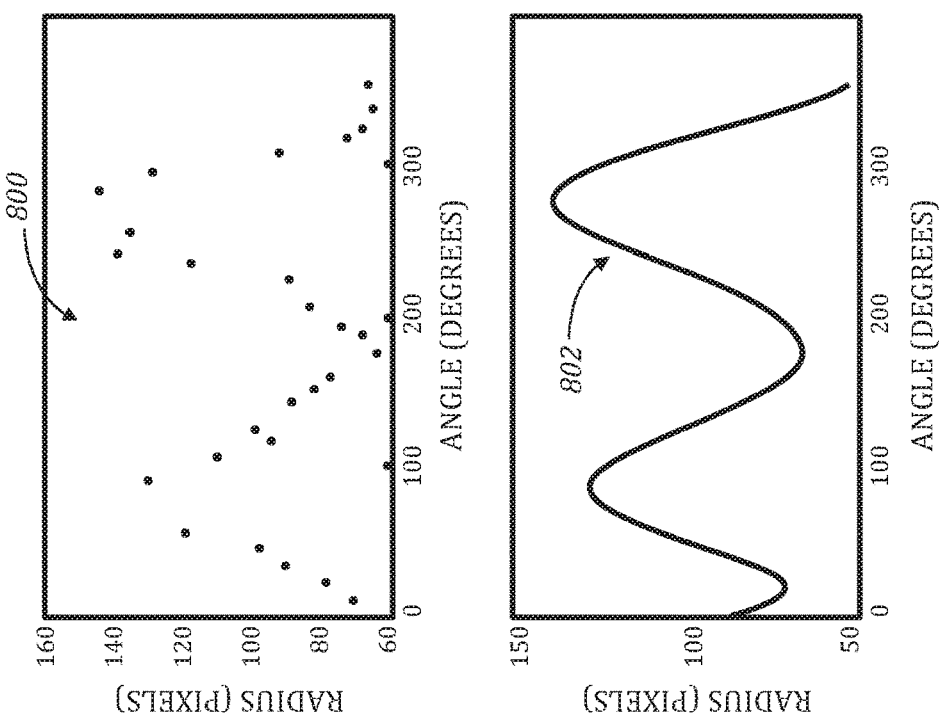
FIG. 8 shows a graph with points crudely marking the LV inner border, and a graph with these points interpolated using a $6^{th}$-order polynomial.

The interpolation may be made at pre-defined angles, such as, for example, every 12 degrees. FIG. 8 shows a graph with the points 800 extracted earlier, which mark the inner border crudely, and a graph with the computed $6^{th}$ order polynomial 802. As may be seen, the $6^{th}$ order polynomial 802 defines points 800, quite surprisingly, fairly accurately.

Steps 102-116 of FIG. 1 lay out the present method 100 for automatic LV inner border detection. Method 100 may be applied to the end-diastole echocardiogram as well as to the end-systole echocardiogram, in order to calculate the ejection fraction (EF) measure, which indicates the global systolic function of the LV by assesing the percentage of blood ejected from the LV during the systole. The ejection fraction of each plane may be calculated, using the widely-accepted Simpson method of discs as follows:

$$EF = \frac{EDV - ESV}{EDV} \times 100 \quad (9)$$

where is EDV is the end-diastolic volume and ESV is the end-systolic volume. An EF of 55% or above is usually considered normal.

The Biplane method may be used to determine EDV, ESV and EF as a combination of the four chambers and two chambers planes, according to:

$$V = \frac{\pi}{4}\sum_{i=1}^{20} a_i b_i \frac{L}{20} \quad (10)$$

where V is the volume, L is the ventricular length, a is the diameter in the four chamber plane and b is the diameter in the two chambers plane. See Roberto M. et al. "*Recommendations for chamber Quantification: A Report from the American Society of Echocardiography's Guidelines and Standards Committee and the Chamber Quantification Writing Group, Developed in Conjunction with the European Association of Echocardiography, a Branch of the European Society of Cardiology*", J Am Soc Echocardiogr, vol. 18, pp. 1440-1463, 2005.

However, the automatic LV inner border detection method laid out above may serve as the basis to gaining insight into additional cardiac factors of great significance. Accordingly, method 100 may include one or more of the following additional steps:

In a block 118, once the inner border is detected, the LV volume may be calculated, for instance using the Simpson method. Next, in a block 120, the defined LV border may be tracked over consecutive echocardiograms of a same cardiac cycle (or, if desired, of more than one cycle), up to an end-systole echocardiogram, so as to define the border also in these echocardiograms. The tracking may be a cost-effective way, at least from the aspect of computational time, of detecting the inner border across the following echocardiograms of the same cycle; the alternative would be to repeat the entire detection process for each and every echocardiogram, which may be inefficient given the fact that typical ultrasound equipment captures between 25 and 100 frames (echocardiograms) per second.

The tracking is optionally performed using the pyramidal optical flow method (see J. Y. Bouguet, "*Pyramidal implementation of the Lucas-Kanade feature tracker, description of the algorithm*", Technical report, Intel Corporation Research Labs, 1994), where the current contour position is used as an input for contour detection in the successive image, under the assumption that the movement is small enough to retain similarity between regions around edge points. Hence, the relatively complex border detection process may be performed once, and its product is "extended" to the following echocardiograms by way of tracking the small, accumulative changes along the cardiac cycle.

In the tracking, when I(x,y) and J(x,y) are two successive echocardiograms from an examination sequence and b=[$b_x$, $b_y$] is a border point on the first image, a border point $b_s$=[$b_x$+$v_x$, $b_y$+$v_y$] is found in the second image such that I(b) and J(b+v) are similar in their two-dimensional neighborhood, defined as W($w_x$,$w_y$). Therefore, d=[$d_x$ $d_y$] is the optical flow at (x,y) which minimizes the sum of squared differences:

$$e(\bar{v}) = \sum_{x=b_x-w_x}^{b_x+w_x} \sum_{y=b_y-w_y}^{b_y+w_y} (I(x,y) - J(x+v_x, y+v_y))^2 \quad (11)$$

The velocity and direction of LV contraction changes along the cardiac cycle. In addition, different LV wall segments move with different velocities. The pyramidal implementation enables the use of a small local window which is beneficial for tracking accuracy and the capture of higher motion velocities by using lower resolution images recursively computed by the Gaussian pyramid.

The outliers of the resulting border points may be filtered according to calculated errors, and edge linking is performed in Cartesian coordinates, where the inner border of each LV wall is modeled by a polynomial shape model. Optionally, in the four chamber view, the septal side of the LV is interpolated by a $4^{th}$-order polynomial, and the inner border at a lateral side of the LV is interpolated using parabolic interpolation. In the two chambers view, the inferior wall is optionally interpolated by a $4^{th}$-order polynomial and the anterior wall is interpolated using parabolic interpolation. These interpolations have been found, quite surprisingly, to define the LV wall, for example the septal and lateral walls of the LV, respectively, with great accuracy.

Figure 9:
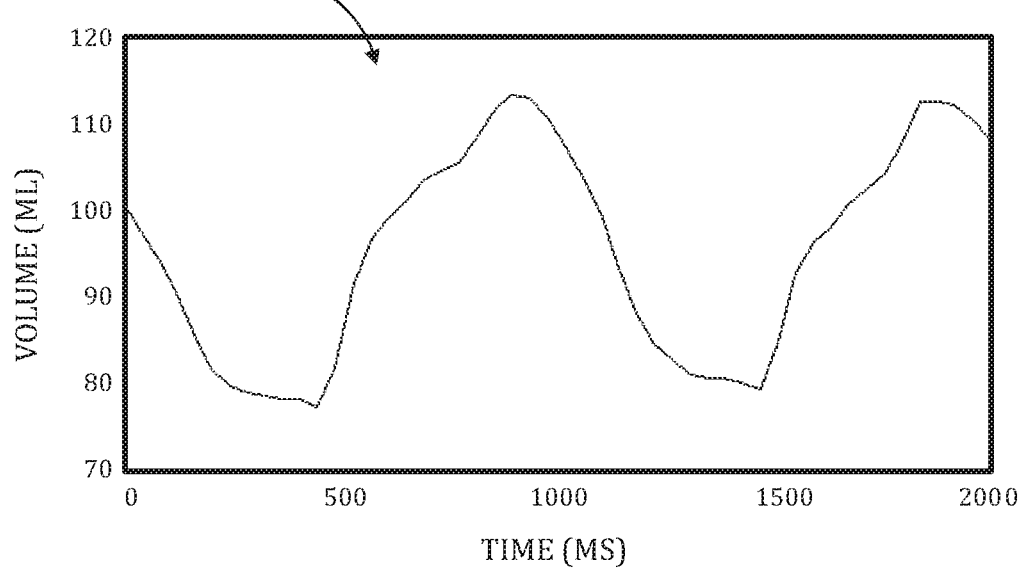
FIG. 9 shows a volume curve of the LV over time.

Having the inner LV border defined for the end-systole and end-diastole echocardiograms, enables the calculation of the EF, which is commonly used by cardiologists for global cardiac evaluation. In a block 122, a volume curve of the LV is optionally constructed, based on LV volume calculated, optionally using the Simpson method, for every echocardiogram. FIG. 9 shows such as exemplary volume curve 900, which illustrates the LV volume in milliliters as a function of time.

Figure 10:
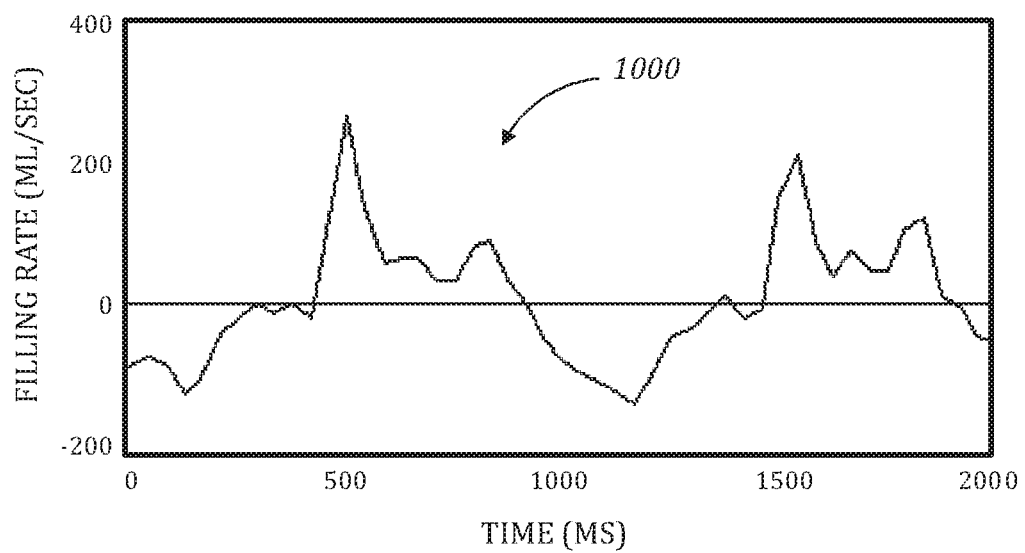
FIG. 10 shows a filling rate curve of the LV, based on the volume curve.

In a block 124 of FIG. 1, a filling rate curve may be computed, based on the volume curve of the previous step. The filling rate, namely, is a derivative of the volume curve. FIG. 10 shows such an exemplary filling rate curve 1000, which illustrates the LV filling rate in milliliters per second as a function of time.

Figure 11:
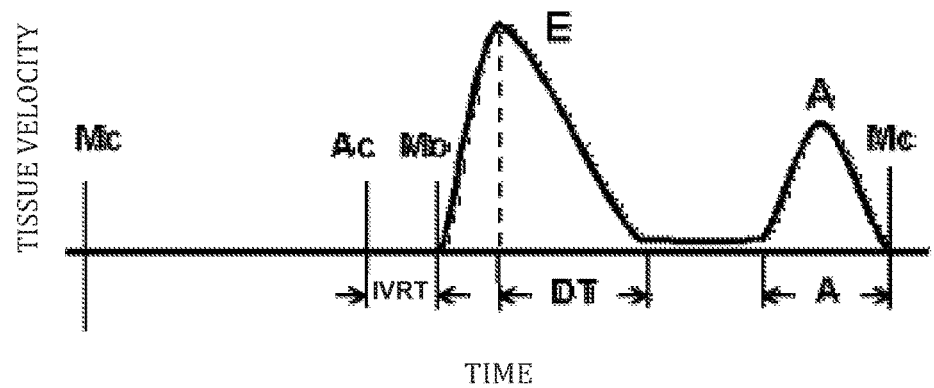
FIG. 11 shows a visual representation of common diastolic function parameters.

Filling rate curve 1000 may serve as a basis for computation of global diastolic and systolic function parameters. As to the global diastolic parameters, FIG. 11 shows a visual representation of the ones which may be directly derived from the filling rate data. These include: Rapid filling peak velocity ("E"), which is the highest velocity measured during the diastole.

Secondary peak velocity ("A"), which is measured during atrial contraction.
E/A ratio.
Acceleration time to E, which is the time it takes the heart to reach E from the end-systole ("Mo").
Deceleration time from E ("DT"), which is the time it takes the heart to finish the diastole, starting from E.
Isovolumetric relaxation time ("IVRT"), which is the time between aortic valve closure and mitral opening, during which the ventricular muscle decreases its tension without lengthening, so that ventricular volume remains unaltered.

Accordingly, one or more of these global diastolic function parameters may be computed, in a block 126 of FIG. 1, based on the filling rate curve.

In a block 128, one or more global systolic function parameters may be computed, based on the filling rate curve. These may include, for example: End-diastole volume (EDV), end-systole volume (ESV), ejection fraction (EF), stroke volume (SV) and the like. Stroke volume is the product of subtracting the ESV from the EDV.

In a block 130, regional LV wall motion may be evaluated. Optionally, the evaluation is performed by computing an angular displacement curve of the detected LV borders. The evaluation of regional wall motion is of great importance, as patients with ischemic heart disease (IHD) usually have segmental rather than global wall contraction abnormalities.

By tracking the previously-detected LV inner border and extracting its polar coordinates over at least one cardiac cycle, an angular displacement curve is formed, representing the radial distance ρ (from a center point of the LV to a point on the border) for a plurality of defined angles θ over time. The angles are arbitrarily defined; for example, in the four chambers view, the mid setpal may be at 0 degrees, the apex may be at 90 degrees, the mid lateral at 180 degrees and the mitral valve at 270 degrees.

Figure 12:
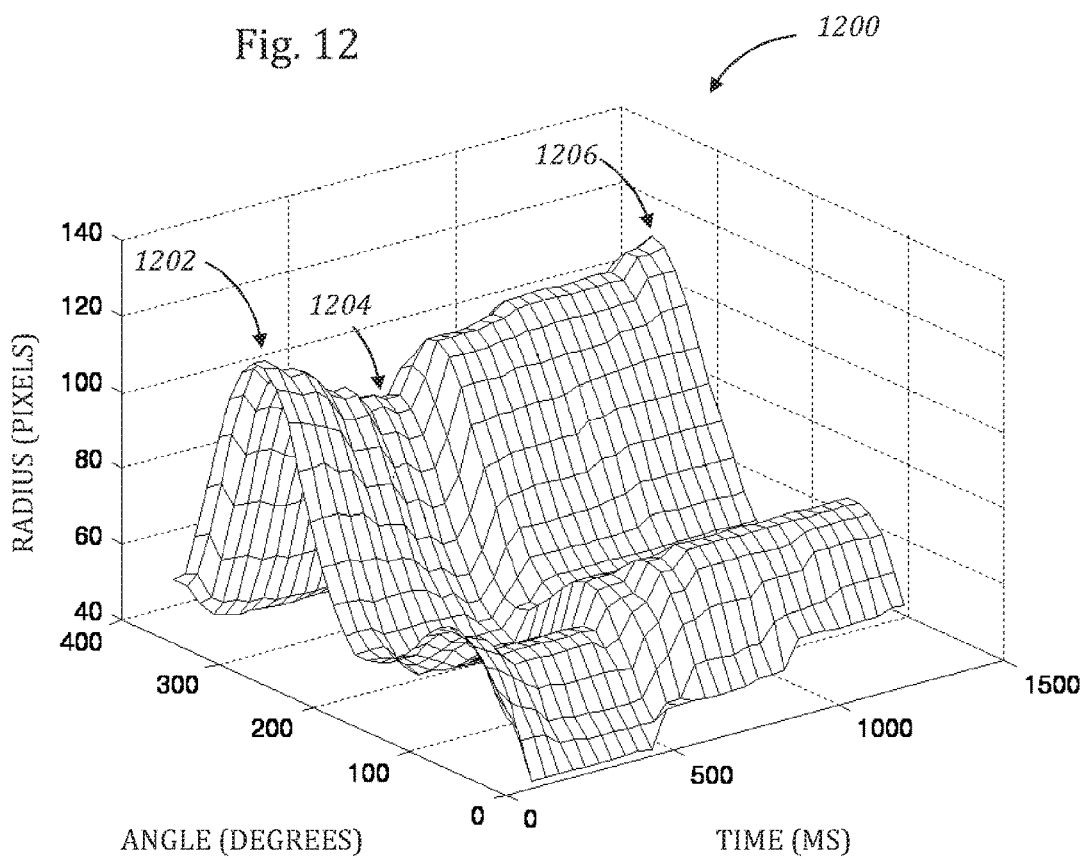
FIG. 12 shows an angular displacement curve, indicating radius as a function of angle and time.
Figure 15:
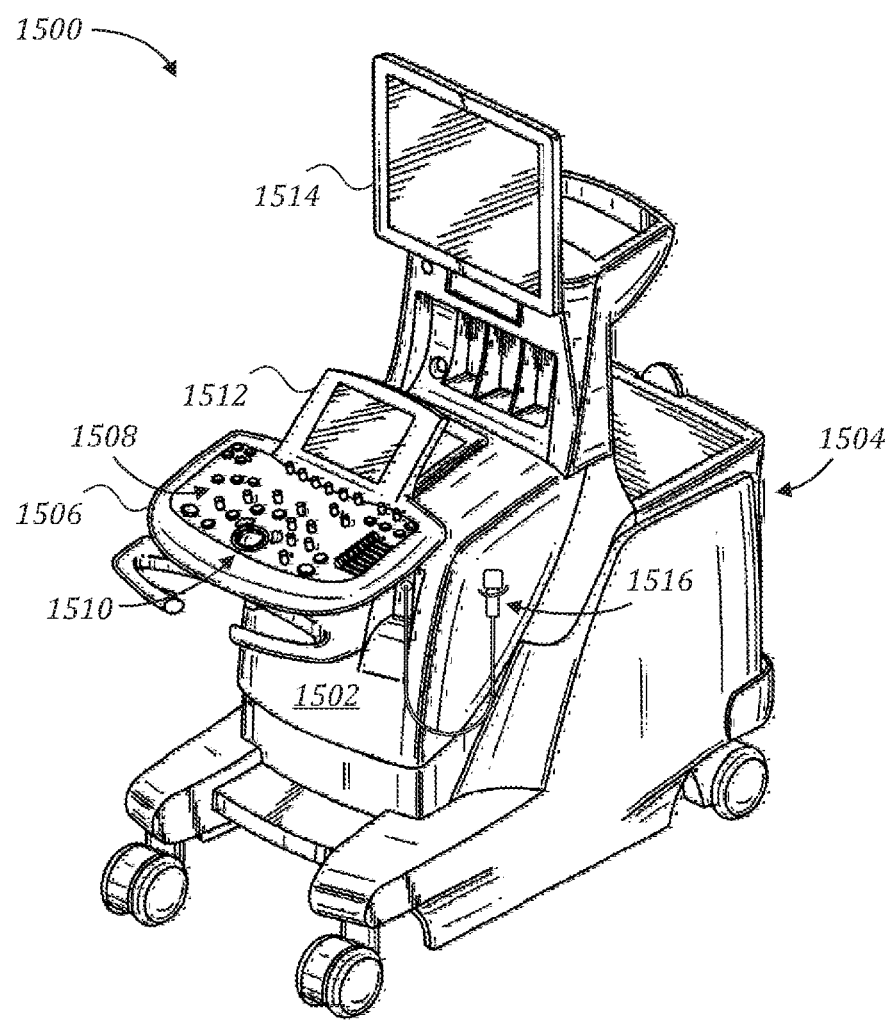
FIG. 15 shows an ultrasonic imaging system.

FIG. 12 shows an exemplary angular displacement curve 1200, indicating radius (in pixels) as a function of angle and time. A first end-diastole 1202 is demonstrated at approximately 100 ms, an end-systole 1204 at about 500 ms, and a second end-diastole 1206 at about 1500 ms.

Furthermore, a comparison may be made between angular displacement curves of the systole and of the diastole. When these curved are overlaid, the differences in segmental motion are more easily perceived. FIG. 13 shows an exemplary overlay 1300 of a diastole displacement curve (continuous line) and a systole displacement curve (dashed line). As before, the mid septal area 1302 is at 0 degrees, the apex area 1304 is at 90 degrees, the mid lateral area 1306 at 180 degrees and the mitral valve area 1308 at 270 degrees. Generally, when comparing these diastole and systole displacement curves represented in polar coordinates, impaired separation along the radial direction usually indicates abnormal wall motion.

Back to FIG. 1, in a block 132, the angular displacement curve may be derived, yielding an indication of tissue velocity.

Specifically, in a block 134, in order to analyze LV wall velocity at a certain point (also "segment" or "region"), the angular displacement curve is derived at this point and over multiple echocardiograms (optionally over at least one cardiac cycle or a portion thereof). By way of example, FIG. 14 shows an angular displacement derivative 1400 over time, of a point 1402 on the LV inner border located at the bottom lateral side. Similar derivatives may be calculated for any other point on the inner border for which regional analysis is required.

Lastly, in a block 136 of FIG. 1, one or more additional global diastolic function parameters, also referred to as "TDI (Tissue Doppler Imaging) parameters", may be calculated based on the tissue velocity calculated at the lateral side mitral annulus. These parameters normally require the use of Doppler ultrasound, but are advantageously calculated here based on regular echocardiograms. FIG. 14 shows such parameters, which are indicative of global diastolic function. An "Aa" parameter is shown at 1404, and an "Ea" parameter at 1406, shown in FIG. 14.

Figure 16:
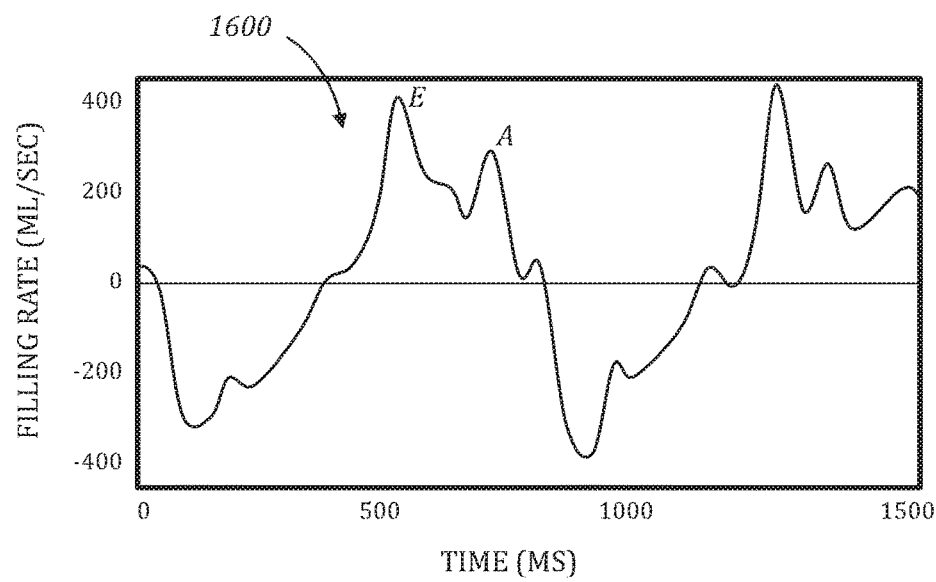
FIG. 16 shows a filling rate curve exhibiting a normal E/A ratio.

Reference is now made to FIG. 16, which shows an exemplary ultrasonic imaging device 1600 including a processing unit (hidden behind 1602) configured to perform some or all of the steps of method 100 (FIG. 1).

Processing unit 1602 incorporates at least a processor and a computer-readable medium or article (not shown) which stores a set of instructions that, when executed by a processor of the processing unit, cause the processing unit to perform a method and/or operations in accordance with embodiments of the invention. The computer-readable medium or article may include, for example, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The instructions may include any suitable type of code, for example, source code, compiled code, interpreted code, executable code, static code, dynamic code, or the like, and may be implemented using any suitable high-level, low-level, object-oriented, visual, compiled and/or interpreted programming language, such as C, C++, C#, Java, BASIC, Pascal, Fortran, Cobol, assembly language, machine code, or the like.

Unless specifically stated otherwise, as apparent from the present discussions, it is appreciated that discussions utilizing terms such as "processing", "computing", "calculating", "determining", or the like throughout the specification, refer to the action and/or process of an ultrasonic imaging device such as device 1600, or a similar electronic computing device, that manipulate and/or transform data represented as physical, such as electronic, quantities within the computing system's registers and/or memories into other data similarly represented as physical quantities within the computing system's memories, registers or other such.

Ultrasonic imaging device 1600 may include a platform, such as a cart 1604. A user console 1606 may include an input device such as keys 1608, a pointing device 1610, and/or the like. One or more screens 1612 and 1614 may be used to display information to the user, such as various outputs of method 100 of FIG. 1. An ultrasonic probe 1616, which acquires echocardiograms, may be connected via cable to processing unit 1602.

Those of skill in the art will recognize that ultrasonic imaging system 1600 is given here merely as an example. A different ultrasonic imaging system, such as a portable ultrasound device or another device, may be similarly suitable to carry out method 100 of FIG. 1. In addition, a general-purpose computer or a CPACS (Cardiac Picture Archiving and Communication System) workstation may be used to carry out method 100 of FIG. 1 offline, by receiving echocardiograms which were previously-acquired by an ultrasonic imaging system.

EXPERIMENTAL RESULTS

Experiment 1

Automatic EF evaluation of a patient with normal global LV systolic function was performed: EF=75%. EDV, ESV and EF results are summarized in Table 2, which compares the present automatic method with manual tracing done by an expert:

TABLE 2

|  | EDV (ml) | ESV (ml) | EF (%) |
|---|---|---|---|
| Expert | 96 | 24 | 75 |
| Algorithm | 99 | 25 | 74 |

Experiment 2

Automatic EF evaluation of a patient previously diagnosed with severely reduced global LV systolic function and dilated LV: EF=25%. EDV, ESV and EF results are summarized in Table 3, which compares the present automatic method with manual tracing done by an expert:

TABLE 3

|  | EDV (ml) | ESV (ml) | EF (%) |
|---|---|---|---|
| Expert | 253 | 189 | 25 |
| Algorithm | 251 | 175 | 30 |

Experiment 3

Automatic, global diastolic function evaluation of a patient previously determined to have normal global LV diastolic function was performed: A filling rate curve 1600 (FIG. 16) exhibited a normal E/A ratio.

Experiment 4

Figure 17:
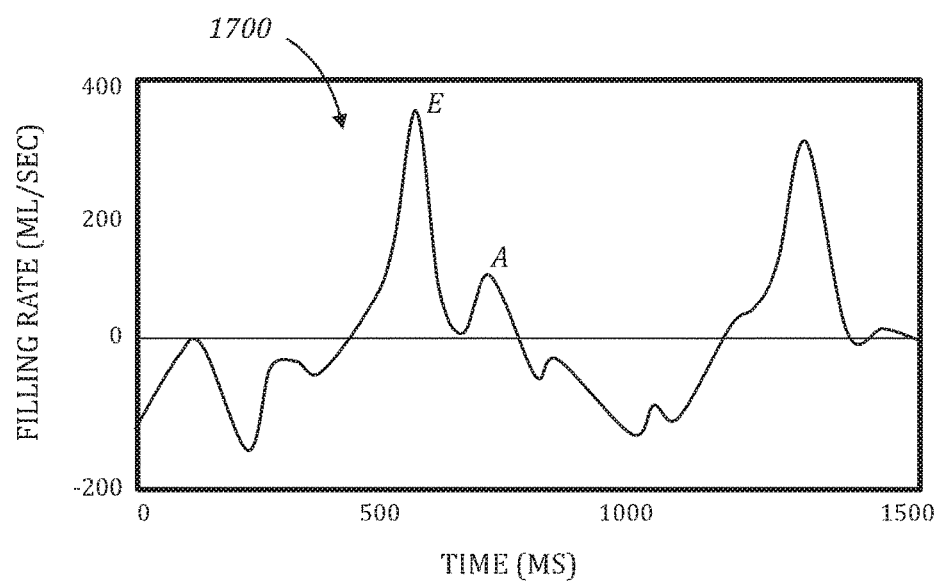
FIG. 17 shows a filling rate curve exhibiting an elevated E/A ratio.

Automatic, global diastolic function evaluation of a patient with impaired diastolic function was performed: A filling rate curve 1700 (FIG. 17) exhibited an elevated "E"/"A" ratio.

Experiment 5

Figure 18:
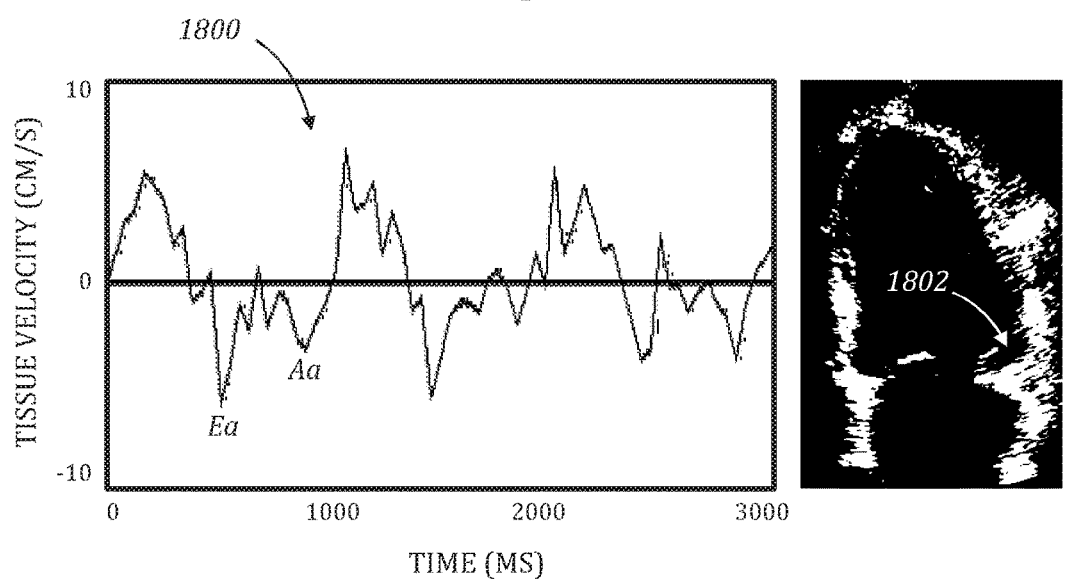
FIG. 18 shows an angular displacement derivative at the mitral annulus, exhibiting Ea and Aa waves with a normal pattern.

Automatic, global diastolic ("TDI") function evaluation of a patient previously determined to have normal global diastolic function: An angular displacement derivative 1800 (FIG. 18) was calculated at the mitral annulus 1802. "Ea" and "Aa" waves exhibited normal pattern.

Experiment 6

Figure 19:
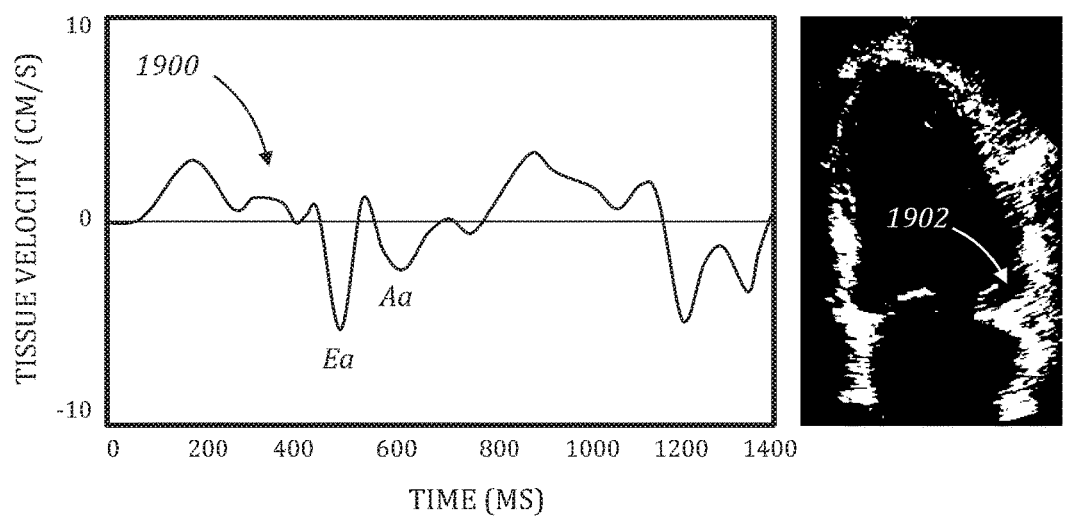
FIG. 19 shows an angular displacement derivative at the mitral annulus, exhibiting Ea and Aa waves with reduced velocity pattern.

Automatic diastolic function evaluation of a patient previously diagnosed with impaired diastolic function: An angular displacement derivative 1900 (FIG. 19) was calculated at the mitral annulus. "Ea" and "Aa" waves exhibited reduced velocity pattern.

Experiment 7

Figure 20:
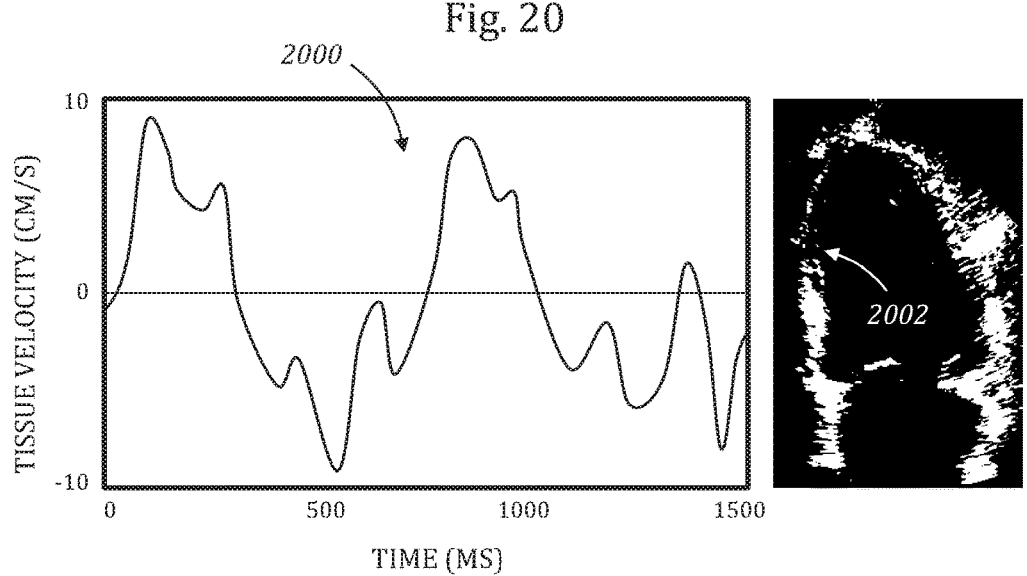
FIG. 20 shows an angular displacement derivative at the septal region, exhibiting normal patterns of the systolic and diastolic velocities.

Automatic segmental wall motion evaluation of a patient previously determined to have normal sectional LV (four-chamber apical view) function was performed: An angular displacement derivative was calculated for multiple regions: Inferior septal, septal, apex, lateral and antero lateral. As an example, the angular displacement derivate for the septal region 2002 is shown at 2000 (FIG. 20). The systolic and diastolic tissue velocities exhibited normal pattern.

Experiment 8

Figure 21:
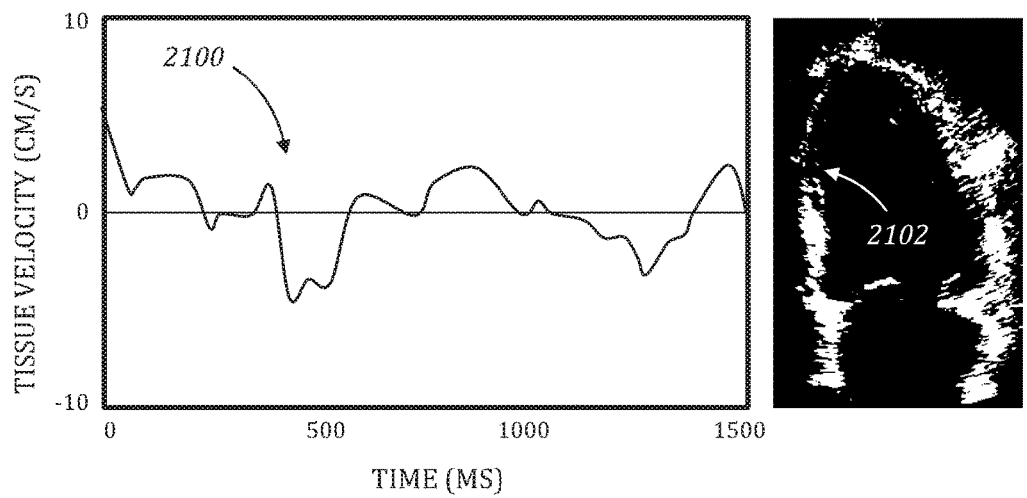
FIG. 21 shows an angular displacement derivative at the septal region, exhibiting severely reduced systolic and diastolic tissue velocities.

Automatic segmental wall motion evaluation of a patient previously diagnosed with general hypokinesis (four-chamber apical view) was performed: An angular displacement derivative was calculated for multiple regions: Inferior septal, septal, apex, lateral and antero lateral. As an example, the angular displacement derivate for the septal region 2102 is shown at 2100 (FIG. 21). The systolic and diastolic tissue velocities were shown to be severely reduced.

Experiment 9

Automatic EF evaluation of a patient with normal global LV systolic function was performed: EDV, ESV and EF results are summarized in Tables 4-6, which compare the present automatic method with manual tracing done by an expert: the four chambers plane (Table 4), the two chambers plane (Table 5) and the Biplane (Table 6):

TABLE 4

|  | EDV (ml) | ESV (ml) | EF (%) |
| --- | --- | --- | --- |
| Expert | 120 | 33 | 72 |
| Algorithm | 96 | 27 | 72 |

TABLE 5

|  | EDV (ml) | ESV (ml) | EF (%) |
| --- | --- | --- | --- |
| Expert | 112 | 35 | 68 |
| Algorithm | 97 | 26 | 73 |

TABLE 6

|  | EDV (ml) | ESV (ml) | EF (%) |
| --- | --- | --- | --- |
| Expert | 116 | 35 | 69 |
| Algorithm | 98 | 29 | 69 |

In the description and claims of the application, each of the words "comprise" "include" and "have", and forms thereof, are not necessarily limited to members in a list with which the words may be associated.

What is claimed is:

1. A method for automatic left ventricular inner border detection, the method comprising:
   performing segmentation on an echocardiogram by segmenting the echocardiogram simultaneously with pixel mapping using piece-wise histogram equalization, wherein the piecewise histogram equalization comprises transforming a pixel intensity histogram of a homogenous regions of the echocardiogram into an equalized histogram having an optimal uniform distribution of intensities, and assigning new intensity values to pixels of the homogenous regions of the echocardiogram based on said equalized histogram, thereby obtaining a multi-level image map having at least three uniformly distributed intensity levels, wherein a first intensity level represents blood, a second intensity represents noise and/or edges and a third intensity level represents myocardium;
   converting the multi-level image map into a binary image by attributing pixels of one or more darker levels of the multilevel image map to the left ventricular cavity and pixels of one or more lighter levels of the image map to the myocardium;
   identifying edges in the binary image;
   applying a radial filter to the edges of the myocardium in the binary image to extract an approximate inner border of the left ventricular cavity and to separate the inner border from the outer border; and
   performing shape modeling on the approximate inner border to complete representation of the left ventricular inner border, wherein the shape modeling is a polynomial shape modeling.

2. The method of claim 1, further comprising, automatically detecting a region of interest in the echocardiogram, prior to performing the image mapping, wherein the region of interest encloses the left ventricle.

3. The method of claim 2, wherein the automatic detection of the region of interest comprises:
   producing an inverted binary version of the echocardiogram;
   computing a column histogram of white pixels in the inverted binary version; and
   defining an area delimited between two minimum points of the column histogram as the region of interest.

4. The method of claim 1, further comprising defining the homogeneous regions of the echocardiogram based on an entropy threshold value.

5. The method of claim 4, wherein the defining of the homogenous regions further comprises determining a central axis of the left ventricle and dividing the left ventricle appearing in the echocardiogram into a plurality of rectangular segments situated on lateral/anterior and septal/inferior sides of the central axis.

6. The ultrasonic imaging device according to claim 1, wherein the polynomial shape modeling comprises a sixth-order polynomial interpolation performed on polar coordinates of the approximate inner border of the left ventricle.

7. The ultrasonic imaging device according to claim 6, wherein the polynomial shape modeling further comprises a fourth-order polynomial interpolation on the approximate inner border at a septal/inferior side of the left ventricle, and second-order interpolation on the approximate inner border at a lateral/anterior side of the left ventricle.

8. The method of claim 1, wherein the echocardiogram comprises an apical view echocardiogram.

9. The method according to claim 8, wherein the apical view comprises a four-chamber apical view.

10. The method of claim 9, wherein the multi-level image map comprises a 3-level image map, and wherein the one or more darker levels of the image map comprise two darker levels and the one or more lighter levels of the image map comprise one lighter level.

11. The method of claim 8, wherein the apical view comprises a two-chamber apical view.

12. The method of claim 11, wherein the multi-level image map comprises a 3 to 5-level image map.

13. An ultrasonic imaging device, comprising:
   an ultrasonic probe configured to acquire an echocardiogram; and
   a processing unit connected to said probe, said processing unit configured to:
      performing segmentation on an echocardiogram by segmenting the echocardiogram simultaneously with pixel mapping using piece-wise histogram equalization, wherein the piecewise histogram equalization comprises transforming a pixel intensity histogram of a homogenous regions of the echocardiogram into an equalized histogram having an optimal uniform distribution of intensities, and assigning new intensity values to pixels of the homogenous regions of the echocardiogram based on said equalized histogram, thereby obtaining a multi-level image map having at least three uniformly distributed intensity levels, wherein a first intensity level represents blood, a second intensity represents noise and/or edges and a third intensity level represents myocardium;

converting the multi-level image map into a binary image by attributing pixels of one or more darker levels of the multilevel image map to the left ventricular cavity and pixels of one or more lighter levels of the image map to the myocardium;

identifying edges in the binary image;

applying a radial filter to the edges of the myocardium in the binary image to extract an approximate inner border of the left ventricular cavity and to separate the inner border from the outer border; and performing shape modeling on the approximate inner border to complete representation of the left ventricular inner border, wherein the shape modeling is a polynomial shape modeling.

14. The ultrasonic imaging device of claim 13, further comprising defining homogeneous regions in the echocardiogram, based on an entropy threshold value.

15. The ultrasonic imaging device of claim 13, wherein the echocardiogram comprises an apical view echocardiogram.

16. The ultrasonic imaging device of claim 15, wherein the apical view comprises a four-chamber apical view.

17. The ultrasonic imaging device of claim 13, wherein said processing unit is further configured to automatically detect a region of interest in the echocardiogram prior to performing the image mapping, wherein the region of interest encloses the left ventricle.

18. The ultrasonic imaging device of claim 17, wherein the automatic detection of the region of interest comprises:
    producing an inverted binary version of the echocardiogram;
    computing a column histogram of white pixels in the inverted binary version; and
    defining an area delimited between two minimum points of the column histogram as the region of interest.

* * * * *